US005792175A

United States Patent [19]

Yoo

[11] Patent Number: 5,792,175

[45] Date of Patent: Aug. 11, 1998

[54] RING

[76] Inventor: Tae-Woo Yoo, 807, 1-Dong, Hanyang Apt, 32-5, Banpo-Dong, Seocho-Ku, Seoul, Rep. of Korea

[21] Appl. No.: 341,472

[22] Filed: Nov. 17, 1994

[30] Foreign Application Priority Data

Jan. 25, 1994 [KR] Rep. of Korea .................... 1994-1321

[51] Int. Cl.$^6$ .................................................. A61B 17/00

[52] U.S. Cl. ............................ 606/204; 601/134; 63/1.1; 63/15

[58] Field of Search .............................. 606/201–204.15, 606/189, 204; 128/907; 601/133, 134, 135, 136–137; 63/5.1, 5.2, 1.1, 2, 15, 15.45, 15.5, 15.8, 11

[56] References Cited

U.S. PATENT DOCUMENTS

| | | | |
|---|---|---|---|
| D. 243,359 | 2/1977 | Neurous | 63/15.5 X |
| 2,310,804 | 2/1943 | Morrison | 601/133 |
| 2,452,286 | 10/1948 | Benjamin | 63/5.2 |
| 2,937,798 | 5/1960 | Morf | 63/5.1 |
| 3,032,032 | 5/1962 | Gifford | 63/11 X |
| 4,122,852 | 10/1978 | Knetsch | 606/204 |
| 5,137,507 | 8/1992 | Park | 128/907 |
| 5,312,350 | 5/1994 | Jacobs | 606/201 |

FOREIGN PATENT DOCUMENTS

| | | | |
|---|---|---|---|
| 408049 | 1/1991 | European Pat. Off. | 606/203 |
| 909616 | 5/1946 | France | 63/11 |
| 2574288 | 6/1986 | France | 601/134 |
| 1482717 | 5/1989 | U.S.S.R. | 128/907 |
| 1595515 | 9/1990 | U.S.S.R. | 601/134 |

*Primary Examiner*—Robert A. Hafer
*Assistant Examiner*—Brian E. Hanlon

[57] ABSTRACT

Ring has serpentine connecting portions between parallel plates on which a plurality of protuberances are formed on the inner surfaces of the plates. The ring promotes the circulation of blood by accupressuring a finger by means of protuberances.

5 Claims, 1 Drawing Sheet

RING

BACKGROUND OF THE INVENTION

The present invention relates to a ring, and more particularly it relates to a ring which can meet the various desires of a user by adding a functional element to the basic object of a ring as ornaments or accessories.

Conventional rings have heretofore been used to show the beauty in the shape of only ornaments or accessories. But, at present, they tend to be contained not only the ornamental element, but the functional element.

SUMMARY OF THE INVENTION

In the light of the foregoing, the present invention has an object to provide a ring, in which a plurality of protuberances are formed in the inner surfaces thereof, substantially closely adhering to a finger, to promote circulation of blood of the finger.

According to the invention, to accomplish the above object, there is provided a ring comprising:

connecting portions secured to both ends of the plates facing each other, and plates on which a plurality of protuberances are formed in the inner surfaces thereof.

BRIEF DESCRIPTION OF THE DRAWINGS

The features of the present invention will be hereinafter explained in detail with reference to the accompanying drawings.

DESCRIPTION OF THE EMBODIMENTS

Referring to drawings, reference mark A designates a ring. Said ring A comprises the connecting portions, 10 10' preferably being made of serpentine elastic members and the plates 12, 12' which secures to both sides of the connecting portions by welding, etc. In said plates a plurality of protuberances 12*a*, 12*a* ' are formed in the inner surfaces thereof which come into substantial contact with the circumference of the finger 20. The plates 12, 12' and the plurality of protuberances 12*a*, 12*a'* are of metal, preferably of silver or aluminum.

Figure 1:
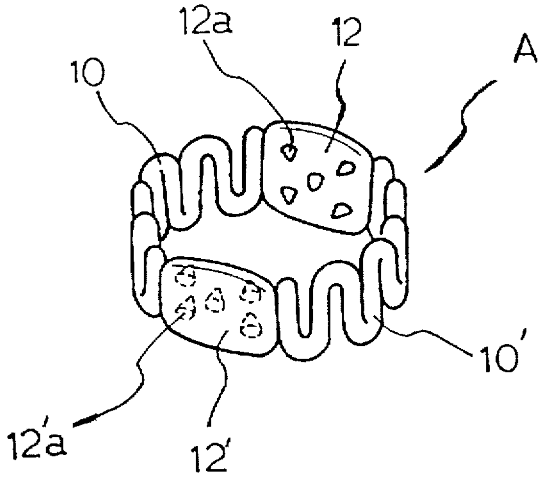
FIG. 1 is a perspective view showing the present invention.
Figure 2:
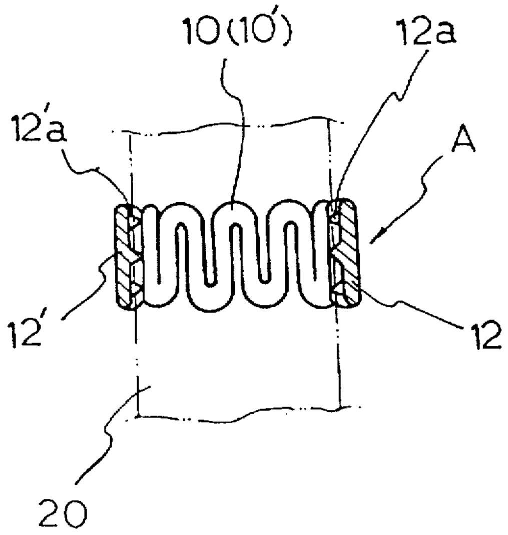
FIG. 2 is a cross-sectional view of FIG. 1.

To summarize the advantages obtained by the invention, the ring A of this invention has the serpentine connecting portions 10, 10' being superior in elasticity, as shown in FIG. 1 and FIG. 2, so that it can be applied without regard to the thickness of fingers. Further, a plurality of protuberances 12*a*, 12*a'* are formed in the inner surfaces of the plates, so that where the ring is put on the finger 20, the circulation of blood of the finger can be promoted by accupressuring by means of protuberances.

As mentioned above, the ring of this invention is a very useful invention in promoting the circulation of blood by putting pressure upon a finger as well having ornamental value.

What is claimed is:

1. A ring having an inner circumference to be worn on a finger, said ring comprising plate means having radially inward facing surface means and a plurality of radially inward directed protuberances extending from said surface means and spaced apart from each other, and serpentine connecting means connected to said plate means and together with said plate means forming said ring.

2. A ring as in claim 1 wherein said plate means comprises a pair of substantially parallel plates and said serpentine connecting means comprises a pair of serpentine connecting members connecting said plates to form said ring.

3. A ring as in claim 1 wherein said plate means are made of metal.

4. Ring as in claim 3 wherein said connecting means are joined to said plate means by welding.

5. Ring as in claim 2 wherein said serpentine connecting means provide sufficient elasticity to provide the ring with an adjustable diameter.

* * * * *